United States Patent [19]
Daugherty et al.

[11] Patent Number: 4,588,398
[45] Date of Patent: May 13, 1986

[54] CATHETER TIP CONFIGURATION

[75] Inventors: Charles W. Daugherty, Xenia, Ohio; Mohammad A. Khan, Sandy, Utah; David J. Lentz, Salt Lake City, Utah; Stephen L. Thoresen, Orem, Utah

[73] Assignee: Warner-Lambert Company, Morris Plains, N.J.

[21] Appl. No.: 649,568

[22] Filed: Sep. 12, 1984

[51] Int. Cl.⁴ .................. A61M 5/00; A61M 25/00
[52] U.S. Cl. .................... 604/265; 604/164; 604/264
[58] Field of Search .............. 604/265, 164, 165–168, 604/264, 280

[56]  References Cited
U.S. PATENT DOCUMENTS

| | | | |
|---|---|---|---|
| 3,598,119 | 8/1971 | White | 604/164 X |
| 3,720,210 | 3/1973 | Diettrich | 604/164 X |
| 3,759,788 | 9/1973 | Gajewski et al. | 604/280 X |
| 4,306,563 | 12/1981 | Iwatshenko | 604/265 |
| 4,317,445 | 3/1982 | Robinson | 604/168 X |
| 4,381,008 | 4/1983 | Thomas et al. | 604/265 |
| 4,392,848 | 7/1983 | Lucas et al. | 604/265 X |

*Primary Examiner*—Stephen C. Pellegrino
*Attorney, Agent, or Firm*—Aaron Passman

[57]  ABSTRACT

A specific configuration for an over the needle catheter having a tapered outer wall and an angled introducer tip is disclosed. The catheter is molded of polyurethane material which is treated with a surface lubricant to ease the over the needle introduction of the catheter after venipuncture. The polyurethane material permits a minimal wall thickness for maximum flow with requisite strength and flexibility characteristics.

6 Claims, 1 Drawing Figure

U.S. Patent
May 13, 1986
4,588,398
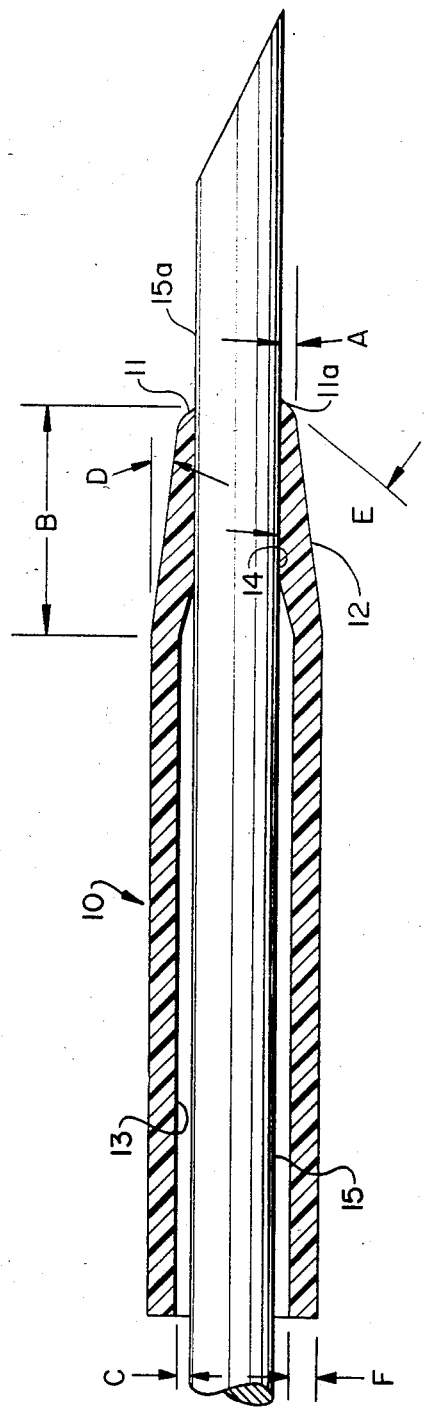

CATHETER TIP CONFIGURATION

BACKGROUND OF THE INVENTION

This invention relates to surgical devices including an over the needle catheter for insertion into the tissues of a body cavity of a patient for the introduction or removal of fluids. Such devices are most commonly intended for intravascular use, particularly for infusion purposes, although various other uses are quite common, such as drainage tubes and so forth. After insertion into the body of a patient the catheter is generally connected by a length of tubing to a container for the fluid which is to be introduced or withdrawn. Since the catheter will normally need to be left in position for at least several hours, it must be resilient and efficiently shaped for the introduction of fluid or removal of fluid.

More specifically the shape of the catheter tip must be such that little trauma is incurred during insertion and once in place the resilient catheter will not damage internal tissues of the blood vessel. Consequently if the catheter is to remain in position for a long period of time, it is more comfortable for the patient if it is made of a relatively soft pliable material. Therefore, the catheter device needs to be included with a removable introducer needle fitted coaxially within the catheter in order to puncture the skin and penetrate the vessel permitting the subsequent over the needle introduction of the catheter into the blood vessel. The introducer needle needs to project slightly beyond the end of the catheter so that shortly after the introducer needle has pierced the skin of the patient the catheter may then pass therewith through the same perforation and once the catheter has been slid along the needle into position the introducer needle can then be removed by coaxially withdrawing the needle from within the inserted catheter.

It has been the problem with devices of this type to produce a catheter material which is suitably resilient and strong and has a tapered tip which permits insertation over the introducer needle. More specifically, the catheter body has to be of high strength and thin wall in order to permit maximum fluid flow yet the tip requires a specific design to permit ease of introduction along with the needle.

It is an object of the present invention to teach a method of providing a catheter configuration which is easily inserted into a patient's blood vessel thereby minimizing trauma and injury.

It is yet another object of present disclosure to illustrate a configuration and a material which permits a high rate of fluid flow and maximum strength with requisite flexibility to be comfortable for the patient during use.

SUMMARY OF THE INVENTION

Disclosed is a specifically configured catheter for an over the needle application. The catheter is specifically configured with a tapered outer wall and an angled introducer tip that has been found to provide the requisite strength, yet permit insertion into a blood vessel with minimal trauma. In order to fashion the specific tapered outer wall and angled tip, a molding process is used. Moreover, the catheter material is a specific polymeric substance treated with a lubricant which permits the ease of use with respect to human tissue thereby facilitating insertion at the puncture site. In addition, the polymeric material is of sufficient strength and resilience to permit the catheter to have a minimal wall thickness thereby allowing maximum flow in any particular gauge. The material which has been found to provide the strength and flexibility characteristics is a polyurethane polymer treated with a surface lubricant. More specifically, the polyurethane polymer exhibits the characteristics of stiffness during insertion yet it becomes more flexible once in place because of the body fluids and temperature.

While scientific measurement or force during actual insertion of the improved catheter with a specially configured tip fashioned from a specific polymer that is surface lubricated is impossible, a laboratory test has been developed. In particular, the test requires that the introducer needle with catheter be perpendicularly punctured through a tautly stretched resilient membrane which is used to simulate the skin. While no means is known for determining exactly whether a specific catheter design will work better than another in a persons skin, the laboratory simulation by perpendicularly puncturing a membrane is of some benefit in determining which needle and catheter design has more resistance during puncture and insertion than another. That is to say that, when the catheter and needle are pressed through a tautly stretched membrane by placing same normal to the plane of the membrane, the force required to make the insertion can be measured. A reading as to the relative effectiveness of a design can be obtained by this technique. The present design has been found to be superior in that the resistance during (1) needle puncture, (2) catheter entry and (3) catheter insertion are all minimized. The membrane used for such testing is a flexible polymer such as polyethylene. Similarly, TYVEK material (produced by Dupont) a 100 percent polyethylene-spun-bonded olefin has been used as an ultimate test. This material is advertised as being difficult to tear, puncture or weaken. Therefore, it makes a difficult to puncture membrane having a relatively low orientation and is excellent for use in ultimately testing the force and drag during insertion of a needle and catheter.

The specific design of the present invention is such that the angled catheter tip has requisite strength but facilitates entry during insertion. The requisite strength tested with TYVEK material means that the edge which first penetrates the test membrane does not fracture, disintegrate, or peal back in a manner which would affect the integrity of the tip or the smoothness of the venipuncture. Only the catheter of the present design has been capable of passing the TYVEK material ultimate test and still have a tapered tip which is easily inserted.

BRIEF DESCRIPTION OF THE DRAWINGS

FIG. 1 is a side elevation view in cross section of the tip portion of a catheter made with the configuration of the present invention. This view is shown enlarged (not necessarily to scale) in order to illustrate the salient features of the geometry.

DETAILED DESCRIPTION OF THE DRAWINGS

Referring to FIG. 1, a catheter 10 is shown. This catheter is molded from polyurethane polymer. The specific material has a high modulus of elasticity with an ultimate tensile strength ranging from 7,500 to 10,500 psi depending upon gauge of tubing tested. The tensile strength is approximately 50 percent higher gauge for gauge than Teflon polymeric materials which are ordinarily used for catheters. Similarly, the elongation is approximately 400 percent verses 260 percent for Teflon materials, whereby the elongation of the polyurethane polymer used in the present catheter is nearly twice that of a similar Teflon polymer catheter.

The rubbery and abrasion resistant nature of the polyurethane material is excellent for producing a very tough tip with a particular edge geometry which can easily be inserted without chafing, fracturing, or peeling back, but it is a problem with respect to manufacture. That is to say that, a means by which the catheters are manufactured cannot be used with a polyurethane material. Using polyolefins and Teflon polymers, the catheter tubing is heated and stretched to get an overall taper and then the end is cut to form a tip. That construction has been used effectively with Teflon material and polyolefins but cannot be used with polyurethane polymers because of its rubbery resilient nature. Polyurethane prevents the effective and clean cutting action necessary. Therefore, the tip used in connection with this preferred catheter has to be molded. That process (molding) has allowed the formation of a specific geometry on the end that is easily inserted, yet has the integrity necessary for proper use.

Specifically, the preferred taper along the outside surface of the hollow tubular catheter body is between 3 degrees 30 minutes and 4 degrees 30 minutes, with a tip chamfer of between 25 to 35 degrees each angle with respect to the axis of the catheter. This geometry results in a height of the chamfered portion of between 0.0015 inches to 0.0025 inches. With the lesser dimension being preferable. While these catheters are made in a variety of different gauge sizes, the wall thicknesses are typically 12 to 13 percent of the outside diameter. Whereas the Teflon polymer catheter runs approximately 15 to 17 percent wall thickness of the outside diameter. The polyurethane material allows a wall thickness reduction of approximately 22 percent and consequently greater flow rates for the same gauge.

Even though the material is tougher, in that it does not have tip integrity problems; it also has the advantage of resisting kinking when bending loads are imposed during insertion. Conversely, the increased temperature (about 37° C.) and moisture inside the blood vessel act to soften the polyurethane thus causing less injury to the patient. In particular, clinical testing has shown that the polyurethane used in the preferred embodiment causes less phlebitis and in dwelling time was lengthened relative to other catheter polymers. That is to say that, the material of the present design has the same stiffness as Teflon material, PVC or polyolefins when it is outside of the human body (about 23° C. and less than 50 percent relative humidity) and is much softer in the blood vessel. Outside the body stiffness allows for the proper flow of fluids through the catheter even though the wall is thin and it is primarily due to the strength (at room temperature and moisture) and resiliency (at body temperature and moisture) of the polyurethane material.

Turning now to FIG. 1, a side view in cross section of the catheter 10, is shown. The geometric configuration which permits the easy insertion over the needle is illustrated in this enlarged view. The catheter 10 is manufactured by molding a polyurethane material and includes a leading edge or chamfer 11 which is angled at between 25 to 35 degrees with respect to the axis of the catheter 10. This angle is shown at "E" on the drawing, FIG. 1. The lead edge 11 has a diametrical thickness of approximately 0.001 to 0.002 inches. This is indicated at "A" on FIG. 1. Similarly, the lead edge 11 angles rearwardly to a tapered portion 12 having a longitudinal distance of "B" the dimensions of which are shown on a chart which follows in this description. The chart illustrates the various dimensional configurations for preferred embodiments of 16 through 24 gauge catheters. The taper angle for portion 12 is between 3 degrees 30 minutes and 4 degrees 30 minutes. This is illustrated as angle "D" in FIG. 1. The inside of the catheter is hollow as shown at 13 and includes an area of reduced inside diameter (radial inwardly) portion 14 designed to provide an interference fit with the outer diameter of needle 15. The needle 15 is a hollow tubular member having a specifically beveled end (not shown) to facilitate skin and venipuncture. This interference fit also lends integrity to the catheter tip 11a which appears at the distal end of the catheter 10 where same meets the outer surface 15a of the hollow needle. The interference fit is due to the thickness "C" (in FIG. 1) and is approximately 0.0001–0.0025 inches and is a function of the inside diameter of the catheter tip. The reduced diameter portion 14 is a function of the way in which the catheter tip is molded being a result of the outer diameter of the mandrel about which the catheter is formed during its manufacture. The interference fit between the tip 11a and the needle 15 ensures support for the tip 11a from the body of the metal needle 15.

| CATHETER DIMENSION FOR PREFERRED EMBODIMENTS AND WITH REFERENCE TO FIG. 1 | | | |
|---|---|---|---|
| | CATHETER DIAMETER | "B" DIMENSION | |
| GAUGE | INCHES | MINIMUM | MAXIMUM |
| 24 | .028 | .035 | .074 |
| 22 | .034 | .051 | .094 |
| 20 | .042 | .064 | .110 |
| 18 | .052 | .083 | .131 |
| 16 | .0685 | .098 | .159 |

This catheter tip 11a is the outermost distal portion of the catheter 10 and is the part thereof which first enters the puncture site produced by the beveled end of needle 15. The lead angle 11 is notably steeper than the tapered portion 12 (with respect to the axis of the catheter 10) whereby the tip has greater integrity than would a slight taper. This geometric integrity prevents cracking, disintegration and peel back.

In use, the catheter body has been found to provide an improved operating surface for entry through the skin and venipuncture. This is not only a result of the geometry of the catheter 10 and its tip 11a but also the material and the lubricant with which the catheter 10 is surface coated. The completed catheter 10 after molding is dipped in a special lubricant which adheres to the surface of the polyurethane. Polyurethane is a difficult material to lubricate and the lubricant had to be specially formulated to wet the surface. In particular, the molded catheter is dipped in a proprietary lubricant having a solvent consisting of 70 percent freon, 30 percent isopropanol mixed with 2 percent Dow Chemical Company's, Dow 4-4159MDX (by weight) and 1.75 percent Dow, 360 silicone, 1,000 CSTKS viscosity (by weight). The lubricant coating is applied by dipping at a rate of two inches per second. Testing has indicated that insertion or shaft drag reduction for the lubricated polyurethane catheter is approximately as good or better than a competitive catheter made from a lubricated Teflon polymeric material even though polyurethane is basically tacky.

The most surprising performance aspect of the polyurethane catheter can be demonstrated in the laboratory with a TYVEK penetration test. No competitive product can pass this test without sustaining considerable tip damage. This phenomenon can be attributed to the thin flash free polyurethane tip with about a 30 degree chamfer angle which provides increased integrity and a proper penetration entry angle. TYVEK cannot be used as a laboratory tool since the competitors product cannot pass this test without sustaining substantial tip damage. While TYVEK is material useful for demonstration purposes, it is not useful for measuring differences in performance. The TYVEK film used for demonstration purposes is Dupont's 1056D material having a film thickness of 0.006 inches.

When penetration testing was done through 0.006 inches polyethylene film the results which follow were obtained. As pointed out, the film is stretched taut and the needle and catheter are perpendicularly inserted through the film with force measurements being taken in grams necessary to penetrate the polyethylene film. The following charts indicate results obtained between the catheter of the present invention in various sizes, a previous catheter of applicant's, assignee, and two leading competitors catheters. These results clearly indicate the improvement in needle tip penetration, catheter taper penetration, and catheter shaft drag for each of the various units tested. In each instance the catheter of the present disclosure (Incisiv catheter) is superior in that the drag or force (in grams) required is measurably less.

| Type | Gauge | | | | |
|---|---|---|---|---|---|
| | 24 | 22 | 20 | 18 | 16 |
| CATHETER TIP PENETRATION | | | | | |
| Incisiv Catheter | 65 (3) | 63 (1) | 77 (4) | 81 (2) | 92 (4) |
| Angiocath Catheter | 111 (5) | 128 (7) | 148 (9) | 161 (12) | 183 (6) |
| Code T | 89 (7) | 98 (17) | 128 (21) | 125 (20) | 121 (20) |
| Code J | 86 (16) | 89 (9) | 93 (11) | 128 (28) | 124 (17) |
| CATHETER TAPER PENETRATION | | | | | |
| Incisiv Catheter | 39 (2) | 39 (1) | 42 (3) | 51 (2) | 56 (3) |
| Angiocath Catheter | 55 (6) | 55 (3) | 65 (6) | 77 (6) | 81 (7) |
| Code T | 44 (3) | 57 (4) | 57 (10) | 84 (20) | 110 (16) |
| Code J | 37 (4) | 42 (2) | 68 (3) | 67 (14) | 71 (6) |
| CATHETER SHAFT DRAG | | | | | |
| Incisiv | 2 (0) | 3 (0) | 4 (1) | 4 (1) | 5 (1) |

-continued

| Type | Gauge | | | | |
|---|---|---|---|---|---|
| | 24 | 22 | 20 | 18 | 16 |
| Catheter | | | | | |
| Angiocath Catheter | 7 (1) | 6 (1) | 8 (1) | 9 (1) | 14 (1) |
| Code T | 4 (1) | 5 (1) | 7 (4) | 9 (2) | 7 (2) |
| Code J | 7 (1) | 7 (1) | 13 (1) | 14 (2) | 21 (2) |

Forces in Grams
Angiocath catheter and Codes T and J are lubricated Teflon material.

While the preferred embodiment of the catheter has been described in detail, those skilled in the art will no doubt appreciate that alterations and modifications can be made to specific details of the geometry and material without departing from the scope of the invention. It is the claims which follow that cover the concept of this invention and should be interpreted accordingly.

What is claimed is:

1. A polymeric catheter for over the needle insertion into a puncture site in the human body comprising:
    an elongated hollow tubular polymeric catheter body molded of polyurethane resin having an ultimate tensile of 7,500 to 10,500 psi depending upon gauge and being treated with surface lubrication,
    a tapered end portion on said body having a first tapering portion with a relatively slight angle of between 3 degrees 30 minutes and 4 degrees 30 minutes, with respect to the axis of said body and terminating with a strong and completely circumferential chamfered lead portion at the penetrating tip to resist catheter tip damage and aid penetration at the puncture site where said lead portion extends outwardly from said first tapering portion to the distal tip of said catheter which first engages the puncture and said chamfered lead portion having a relatively blunt angle of between 25 and 35 degrees with respect to the axis of the catheter.

2. The catheter of claim 1 wherein said chamfered lead portion is approximately 0.001 to 0.002 inches thick.

3. The catheter of claim 1 wherein said polyurethane material has an elongation capability in the range of approximately 150 to 400 percent.

4. The catheter of claim 1 wherein said catheter surface lubrication includes a silicone material.

5. The catheter of claim 1 wherein said polyurethane is relatively stiff at room temperature and humidity and is relatively soft and pliable at the internal temperature and moisture conditions of a human blood vessel.

6. The catheter of claim 1 wherein said hollow tubular body being designed to engage the outer diameter of a hollow needle along its shank and said body has a slightly reduced inside diameter portion of lesser diameter near said tip for a greater interference fit near the end of the needle beneath said chamfered lead portion.

* * * * *